(12) United States Patent
Glagau et al.

(10) Patent No.: US 6,835,554 B2
(45) Date of Patent: Dec. 28, 2004

(54) KIT AND METHOD FOR DETERMINING REDOX STATUS IN URINE

(75) Inventors: Kristian Glagau, Langenfeld (DE); Ralf-Siegbert Hauck, Hilden (DE)

(73) Assignee: Orthomol Pharmazeutische Vertriebs GmbH, Langenfeld (DE)

( * ) Notice: Subject to any disclaimer, the term of this patent is extended or adjusted under 35 U.S.C. 154(b) by 198 days.

(21) Appl. No.: 10/157,455

(22) Filed: May 29, 2002

(65) Prior Publication Data

US 2003/0087330 A1 May 8, 2003

Related U.S. Application Data

(63) Continuation-in-part of application No. PCT/EP00/13187, filed on Dec. 22, 2000.

(51) Int. Cl.$^7$ .......................... C12Q 1/26; G01N 33/50; C07D 209/04
(52) U.S. Cl. .................. 435/25; 435/287.6; 422/56; 548/469
(58) Field of Search ................. 435/29, 810, 287.2, 435/287.3, 287.6, 25; 436/128, 162, 524; 422/56, 61; 548/469

(56) References Cited

U.S. PATENT DOCUMENTS

| | | | |
|---|---|---|---|
| 3,901,657 A | * | 8/1975 | Lightfoot ..................... 422/56 |
| 4,148,611 A | | 4/1979 | Nand et al. |
| 4,670,385 A | | 6/1987 | Babb et al. |
| 5,726,063 A | | 3/1998 | Gerard-Monnier et al. |
| 5,958,714 A | | 9/1999 | Gordon et al. |
| 6,165,797 A | * | 12/2000 | Halstead ..................... 436/128 |

FOREIGN PATENT DOCUMENTS

| | | | |
|---|---|---|---|
| JP | 57 049862 A | | 3/1982 |
| WO | WO99/20396 | * | 4/1999 |

OTHER PUBLICATIONS

Durkee et al. "The Detection of Some Indoles and Related Compounds on Paper Chromatograms" J. Chromat. (1964)13(1): 173–80.*
Arya et al. "Determination of Free Malonaldehyde in Vegetable Oils" J. Food Sci. Technol. (1971) 8(4): 177–80 (abstract only).*
International Search Report, International Application No.: PCT/EP00/13187, International Searching Authority/ European Patent Office.

* cited by examiner

Primary Examiner—Jean C. Witz
Assistant Examiner—Susan Hanley
(74) Attorney, Agent, or Firm—Blackwell Sanders Peper Martin LLP (57) ABSTRACT

A method and corresponding kit for determining the redox status of an organism is provided. The method comprises performing a calorimetric assay of a urine sample by mixing the sample with at least one member of a group of disclosed reagents and an acid and, upon stable color formation, comparing the resulting color to a color scale to indirectly determine the oxidative load, or stress, experienced by that organism. The corresponding kit comprises at least one of the reagents described above, an acid, and a color scale.

34 Claims, 3 Drawing Sheets

KIT AND METHOD FOR DETERMINING REDOX STATUS IN URINE

This is a continuation-in-part of international patent application PCT/EP00/13187 filed Dec. 22, 2000, from which priority is claimed in the present application.

This invention relates to a kit and method for determining redox status in urine. The invention relates in particular to such a kit and such a method in which the determination of redox status can be carried out extremely easily on the basis of the color reaction with a reagent selected from the group of indole derivatives by visual color comparison, i.e., with the naked eye.

BACKGROUND TO THE INVENTION

The human body is exposed to a large number of loads causing free radicals to be produced in the cells of the body, particularly under the present environmental conditions. These loads include, for example, cigarette smoke, car exhaust gases, UV radiation, and various other noxious substances. The free radicals produced, which also include oxygen free radicals, form pathogenic products of degradation, which are able to cause sustained damage to various components within the cells of the body cell in a wide variety of subsequent oxidative reactions. The consequences of this damage include, for example, premature aging, but also serious diseases such as diabetes or cancer.

In order to neutralize, i.e., bind free radicals, which also occur to a limited degree under ideal environmental conditions, the human body has developed a number of systems with an anti-oxidative system. However, these systems are frequently overloaded, among other things, because of lifestyles and the particular environmental situation of the human being, so that free radicals in the body cannot be rendered sufficiently harmless. In such cases, it is necessary to stimulate or support the body's own anti-oxidative systems by eating special food supplements (micro-nutrient preparations from vitamins and trace elements). In such a treatment, the quantity of drugs administered or supplements taken should be adapted to the actual loading of the body with free radicals.

Ideally, the determination of the load exerted by free radicals should be carried out by the patient himself/herself without major expenditure, quickly, and at low cost. Such a determination may therefore be carried out on the basis of urine samples in particular.

SUMMARY OF THE INVENTION

The fundamental objective of this invention is therefore to determine redox status in urine by simple means, i.e., by the naked eye. "Determination of redox status" is defined in this connection as obtaining a quantitative, semi-quantitative, or qualitative statement on the concentration and presence of free radicals in the human body, i.e., on the oxidative loading of the organism. The malonic dialdehyde in the urine serves as an indicator substance for this statement, but other relevant substances can also be recorded, as appropriate.

This objective is achieved according to the invention by a kit for determining redox status in urine, comprising:

(a) at least one reagent selected from the group of compounds with the general formula (I)

(I)

wherein $R^1$ is H or $C_1$–$C_{10}$-alkyl;

and wherein $R^2$ is independently selected from the group consisting of H; $C_1$–$C_{10}$-alkyl; $NH_2$; NHR; $NR_2$; NHCOR; OH; OR; OCOR; SH; SR; F; Cl; Br; $CF_3$; or $CCl_3$, and wherein each R is selected from the group consisting of $C_1$–$C_6$-alkyl;

and wherein $R^3$ and $R^4$ are independently selected from the group consisting of H; $C_1$–$C_{10}$-alkyl; $NH_2$; NHR; $NR_2$; NHCOR; OH; OR; OCOR; SH; SR; F; Cl; Br; CF3; $CCl_3$; $C_6$–$C_{14}$-aryl; $C_6$–$C_{14}$-aryl, wherein the aryl group is substituted by one or more substituents selected from the group consisting of $C_1$–$C_6$-alkyl, NH2, NHR, $NR_2$, NHCOR, OH, OR, OCOR, SH, SR, F, Cl, Br, $CF_3$ and $CCl_3$, and wherein each R is selected from the group consisting of $C_1$–$C_6$-alkyl;

(b) at least one acid; and (c) a color scale for the visual color comparison, where a certain redox status of the urine to be analyzed is assigned to individual colors on the scale.

According to a further embodiment of the invention, a method is also provided for determining redox status in urine, comprising the following stages:

(a) Mixing of a urine sample to be analyzed with (i) at least one reagent selected from the group of compounds with the general formula (I)

(I)

wherein $R^1$ is H or $C_1$–$C_{10}$-alkyl;

and wherein $R^2$ is independently selected from the group consisting of H; $C_1$–$C_{10}$-alkyl; $NH_2$; NHR; $NR_2$; NHCOR; OH; OR; OCOR; SH; SR; F; Cl; Br; $CF_3$; or $CCl_3$, and wherein each R is selected from the group consisting of $C_1$–$C_6$-alkyl;

and wherein $R^3$ and $R^4$ are independently selected from the group consisting of H; $C_1$–$C_{10}$-alkyl; $NH_2$; NHR; $NR_2$; NHCOR; OH; OR; OCOR; SH; SR; F; Cl; Br; $CF_3$; $CCl_3$; $C_6$–$C_{14}$-aryl; $C_6$–$C_{14}$-aryl, wherein the aryl group is substituted by one or more substituents selected from the group consisting of $C_1$–$C_6$-alkyl, NH2, NHR, $NR_2$, NHCOR, OH, OR, OCOR, SH, SR, F, Cl, Br, $CF_3$ and $CCl_3$, and wherein each R is selected from the group consisting of $C_1$–$C_6$-alkyl;

(ii) at least one acid; and (b) after a stable coloration of the sample has been achieved, visual comparison of the coloration of the sample with a color scale, a specific redox status of the urine to be examined being assigned to the individual colors of the scale.

The kit and the method according to the invention are based on a color reaction, which shows the reagent having the formula (I) under acid conditions when mixed with the urine sample to be analyzed. This color reaction results in the formation of a colored dye characteristic of the initial reagent, the intensity of the coloration depending on the oxidative loading of the organism. In this case, the heavier this load, i.e., the higher the concentration of free radicals in the body, the more intensive the coloration. In general, the color of the sample that can be perceived with the naked eye is also influenced by the color of the urine analyzed.

This color reaction is initiated in particular by the presence of malonic dialdehyde in the urine analyzed. Malonic dialdehyde is a product of degradation of certain hydroperoxides, which are formed by the oxidation of unsaturated fatty acids of the cell membrane in the organism. Since oxidative stress results in intensified lipid oxidation of the cell, it also causes an increase in the concentration of malonic dialdehyde in the urine. This increase can be determined by means of the kit and method according to the invention, so that countermeasures can then be taken, depending in particular on the intensity of the load, e.g., measures such as strengthening the anti-oxidative defense by taking suitable vitamins and trace elements and/or altering one's lifestyles (smoking, diet, living/working environment).

The redox status is determined by means of the kits according to the invention, and by the method according to the invention, by mixing together the reagent, the acid, and the urine sample at room temperature, whereupon the coloration stabilizes, depending in particular on the intensity of the oxidative load. The color reaction is generally completed within 15 to 60 minutes, and in preferred embodiments within 15 to 30 minutes. Afterwards, i.e., as soon as the intensity of the coloration stops increasing, this intensity is determined visually, i.e., by the naked eye, by comparison with a color scale. In this case, the color scale consists of a number of discrete color elements, which are arranged according to their intensity and whose colors correspond to the coloration of the sample solution after termination of the color reaction, according to redox status.

DESCRIPTION OF PREFERRED EMBODIMENTS

The reagents with the general formula (I) are indole derivatives. In formula (I), $R^1$, $R^2$, $R^3$, and $R^4$ denote, among other things, an alkyl group with 1 to 10 carbon atoms. Examples of such alkyl groups are methyl, ethyl, n-propyl, iso-propyl, n-butyl, sec-butyl, iso-butyl, tert-butyl, pentyl, and hexyl. Alkyl groups with 1 to 6 carbon atoms are preferred, and those with 1 to 4 carbon atoms are particularly preferred. A particularly preferred alkyl group is the methyl group.

In formula (I), $R^3$ and $R^4$ may also denote an aryl group with 6 to 14, preferably 6 to 10 carbon atoms, among other things. This aryl group may, as appropriate, be substituted by one or more substituents selected from the group consisting of $C_1$–$C_6$-alkyl, $NH_2$, NHR, $NR_2$, NHCOR, OH, OR, OCOR, SH, SR, F, Cl, Br, $CF_3$, and $CCl_3$, in which R denotes $C_1$–$C_6$ alkyl, and where several R groups may optionally be selected independently. A particularly preferred aryl group is phenyl.

In formula (I), $R^2$, $R^3$, and $R^4$ may also denote $NH_2$, NHR, $NR_2$, NHCOR, OH, OR, OCOR, SH, SR, F, Cl, Br, $CF_3$, or $CCl_3$, where R denotes $C_1$–$C_6$-alkyl and where several R groups may optionally be selected independently. These groups are, in particular, substituents with a positive mesomeric effect. A particularly preferred group of this kind is the methoxy group.

Preferred reagents with the general formula (I) are: 2-methyl indole, 1,2-dimethyl indole, 1-methyl indole, 2-phenyl indole, and 1-methyl-2-phenyl indole. These reagents are particularly preferred, for their stability or the long-term storage stability of their solutions and/or for their availability in (highly) pure form.

According to the invention, an acid, which may be inorganic or organic, is used. Suitable acids include, for example, hydrochloric acid, sulphuric acid, phosphoric acid, methane sulphonic acid, citric acid, oxalic acid, trifluoroacetic acid, or trichloroacetic acid. The use of hydrochloric acid is particularly preferred.

The reagent and/or acid may be used in the form of a solution in a suitable solvent. In principle, all solvents, which are miscible with water and do not have a highly toxic action, are suitable. Lower alcohols, such as methanol, ethanol, propanol, isopropanol, or butanol are particularly suitable, but in closed systems acetonitrile, tetrahydrofuran, or hexamethyl phosphoric acid triamide may also be suitable. Ethanol and isopropanol are preferred, the latter being particularly preferred.

When the reagent is used in the form of a solution, its concentration in it is generally 0.1 to 50 mmol/l, preferably 5 to 15 mmol/l, and more preferably 7 to 12 mmol/l.

When the acid is used in the form of a solution, its concentration in it is generally 0.1 to 5 mol/l, preferably 0.5 to 1.5 mol/l, and more preferably 0.9 to 1.2 mol/l.

A solution of hydrochloric acid in methanol, ethanol, or isopropanol is used in preference as an acid, a solution of hydrochloric acid in isopropanol being particularly preferred.

The color scale or color matrix can be set up by preparing model urine solutions with various known concentrations of malonic dialdehyde and various intensities of yellow coloration and carrying out the above-described method on these solutions. The end point colors thus obtained are then reproduced in the form of a one-dimensional scale or a two-dimensional matrix.

Since the coloration of the urine sample analyzed generally also depends on the color of the urine to be analyzed, i.e., its yellow coloration of varying intensity, it is appropriate to supply different color scales for the individual initial urine colors. These scales may, in particular, be arranged in the form of a color matrix, the first line of the matrix containing the urine colors considered, whose correspondence is established initially by comparison with the untreated urine. The color comparison with the sample after the end of the color reaction is then carried out inside the color matrix column, which established by the correspondence of the color of the initial urine.

With regard to the cost of determining the redox status using the kit and method according to the invention, the components required for this, i.e., the reagent and the acid, are supplied and used in such a form that their portioning or handling are simplified as much as possible. In this connection, however, consideration must be given to the fact that solutions of the reagent exhibit a low storage stability under acid conditions, so that the reagent and the acid cannot be brought into contact with each other until shortly before the actual determination is carried out.

According to a particular embodiment of the invention, the reagent or a solution of it is therefore enclosed in a container, thereby separating it from the acid. This container can easily be destroyed or opened by deliberate mechanical action and is arranged so that the reagent comes directly into contact with the acid and/or with a solution of it and/or with the urine sample due to the destruction or opening of the container. The container mentioned may, for example, be a glass ampoule. This glass ampoule may, in turn, be arranged inside a vessel, which contains the acid or a solution of it, and to which the urine sample is fed in order to carry out the determination. The color reaction can then be initiated by breaking the glass ampoule inside the vessel so that the content of the ampoule and the vessel mix together.

Accordingly, the acid, instead of the reagent, can also be enclosed in a separate container, which is arranged as described above and is opened or destroyed correspondingly.

Figure 1:
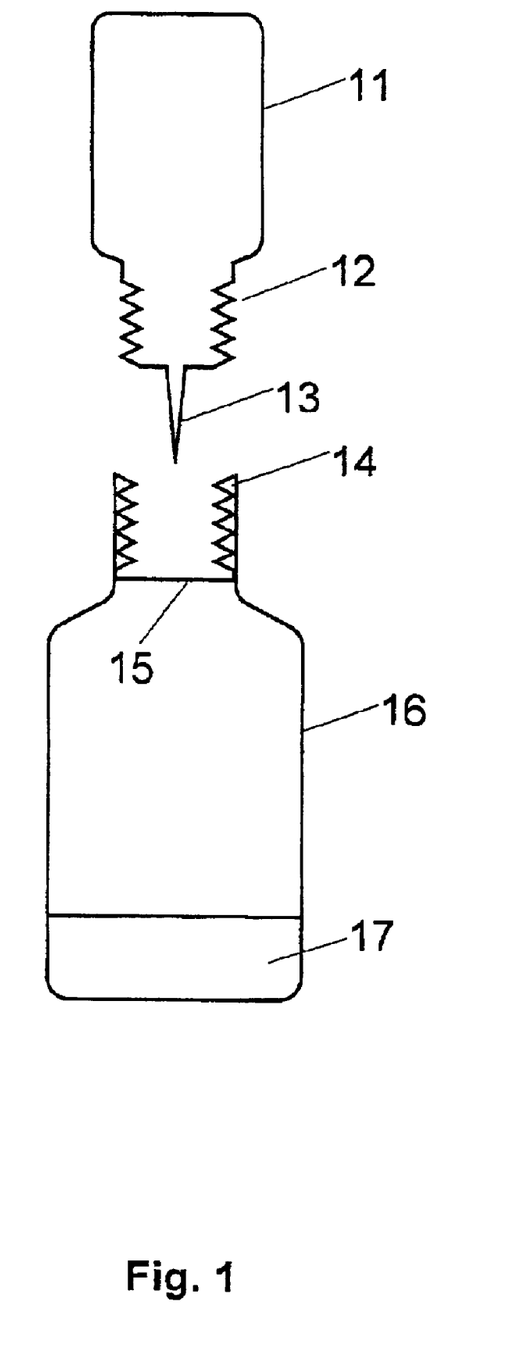
FIGS. 1 to 3 show preferred embodiments of two- or multi-chamber systems that can be used according to the invention.

A further embodiment of the two-chamber system that can be used according to the invention is represented diagrammatically in FIG. 1. The system shown in that figure consists of two vessels 11 and 16, each of which is provided with screw threads 12 and 14 respectively, whereby they can be connected together. During this connection, a membrane 15, with which vessel 16 is sealed, pierces a pointed opening 13 of vessel 11. In vessel 16, there is a reaction component 17 (reagent or acid), while the other component (acid or reagent) is contained in vessel 11, and does not reach vessel 16 until after membrane 15 has pierced it.

Vessel 11 may advantageously be designed as a plastic bottle, which can be compressed for transferring its content into vessel 16. The urine sample to be analyzed may also be sucked into vessel 11, in this case, before it is transferred together with one of the reaction components into vessel 16.

Figure 2:
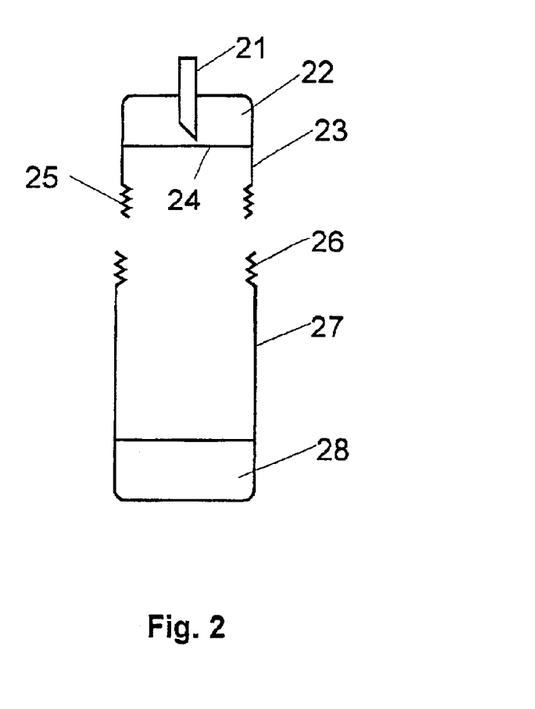

A two-chamber system that can be used according to the invention may also be designed as shown diagrammatically in FIG. 2. The system showed in this figure consists of two vessels 23 and 27, which are provided with screw threads 25 and 26 and can therefore be tightly connected to each other. In vessel 23, a chamber 22, which contains one of the reaction components (reagent or acid), is formed by a membrane 24. Membrane 24 is pierced by pressing pin 21 inwards so that the reaction component contained in chamber 22 comes into contact with the other component 28 (acid or reagent) contained in vessel 27. The urine sample to be analyzed may advantageously be fed into vessel 27 before membrane 24 is pierced, but also after the reagent and acid are mixed together, as appropriate.

In a modification of the system as shown in FIG. 2, pin 21 may also be omitted if the threads and membrane are designed so that the membrane is torn apart when the vessels are screwed together.

Figure 3:
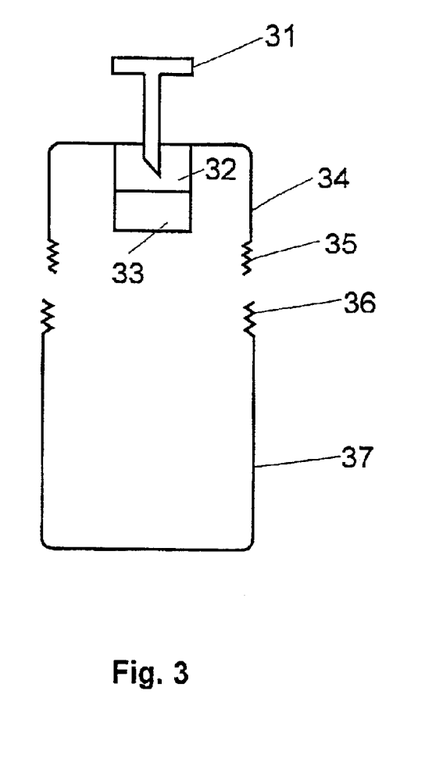

A further advantageous variant of a multi-chamber system that can be used according to the invention is shown in FIG. 3. This system also consists of two vessels 34 and 37, which can be connected together by screw threads 35 and 36. The reagent and the acid are herein contained in two chambers 32 and 33 designed to be connected to vessel 34, and are brought into contact with each other by actuating piston 31. In this system, vessel 37 may advantageously be designed as a beaker used directly for receiving the urine sample.

With regard to the dosing and handling of the reagent, this can be advantageously effected not only in pure form, but also by mixing with a neutral carrier material, such as powder, a tablet, or on a solid carrier (e.g., a plastic strip). The following may be considered neutral carrier substances, given by way of examples: neutral alkali salts, e.g., sodium chloride, or inert carriers of higher density, e.g., $SiO_2$. The weight ratio of reagent to carrier substance is in this case generally 1:0 (pure reagent) to 1:1000, preferably 1:0 to 1:200.

To facilitate the determination of redox status, the kit according to the invention may contain a vessel for directly receiving the excreted urine. This vessel may be designed, for example, in the form of a simple beaker. Furthermore, the kit according to the invention may contain a means of pipetting, for example. This may be used, in particular, for transferring a measured quantity of the urine to be analyzed from the aforementioned vessel for sampling to the vessel in which the color reaction is carried out. Commercially available disposable pipettes may be used, in particular, as means of pipetting.

Moreover, the kit, according to the invention, may contain an analysis vessel in which the color reaction is carried out by mixing together the reagent, the acid, and the urine sample. According to a particularly advantageous embodiment, the color scale may be connected to the analysis vessel so that the sample solution and the individual color elements of the scale are located in the immediately spatial vicinity, so that the color comparison can be carried out immediately, i.e., at a glance.

According to a further advantageous embodiment of the invention, the reagent and the acid are both worked in solid form into a test strip, which can be immersed directly into the sample to be analyzed. In this case, citric acid, oxalic acid, or trichloroacetic acid may be used as the acid.

Figure 4:
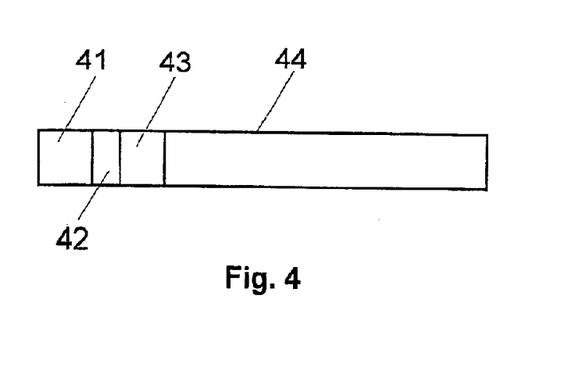
FIGS. 4 to 6 show preferred embodiments of test strips that can be used according to the invention.

A simple embodiment of such a test strip is represented diagrammatically in FIG. 4. In the case of the test strip 44 shown in that figure, the acid is applied in two discrete areas, 41 and 43, between which there is an area 42, which contains the reagent. When the test strip is immersed in the urine sample to be analyzed, the acid diffuses into reagent area 42, where the color reaction takes place. Once this has finished, the color of this area is compared with the color scale.

Figure 5:
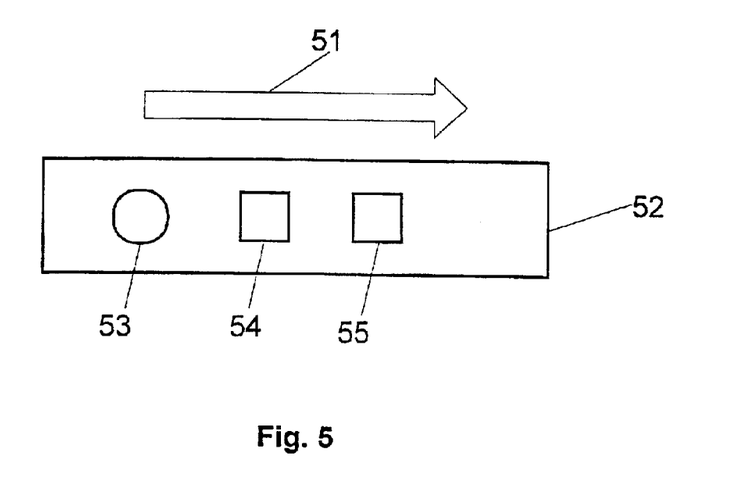

A test strip that can be used according to the invention may also be designed in the form of a test cassette shown diagrammatically in FIG. 5. Cassette 52 contains a fleece strip to which the urine sample is applied in the area of opening 53. The sample then spreads through the strip in the direction indicated by arrow 51. The acid is applied in area 54, and is absorbed by the solution on its way to area 55 containing the reagent, so that the color reaction takes place in area 55. The color comparison can then be carried out through a suitable opening.

Figure 6:
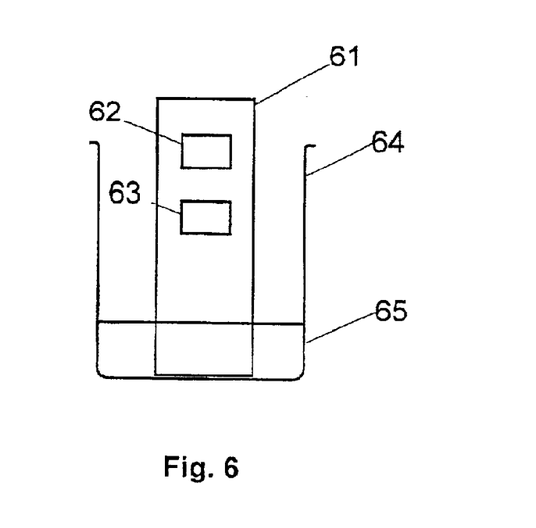

According to the invention, a test strip may also be designed or used as shown diagrammatically in FIG. 6. Here the acid is contained in area 63 and the reagent in area 62 of strip 61. Strip 61 is immersed in urine sample 65 to be analyzed, which is located at the bottom of vessel 64. The sample solution then spreads up and out by capillary forces. In doing so, it passes into area 63, where it absorbs the acid before the color reaction takes place in area 62.

EXAMPLES

This invention is explained in greater detail with reference to the following examples:

Example 1

Determination of Redox Status

According to three different variants, the components (reagent and acid) indicated in the following Table 1 are each mixed in the quantities also indicated in Table 1 with

1 ml of fresh morning urine. The mixture thus obtained is shaken vigorously in a sealed vessel and allowed to stand. After 15 to 20 minutes, the coloration production is compared to the color scale.

TABLE 1

| Variant | Component | Composition | Quantity |
|---|---|---|---|
| 1 | Reagent | 100 mg of 2-methyl indole dissolved in 100 ml of isopropanol | 1 ml |
|   | Acid | 25% aqueous HCl solution | 1 ml |
| 2 | Reagent | 100 mg of 2-methyl indole dissolved in 50 ml of isopropanol | 1 ml |
|   | Acid | 25 ml of 25% aqueous HCl solution, mixed with 50 ml of isopropanol | 1 ml |
| 3 | Reagent | 100 mg of 2-methyl indole mixed with 20 g of sodium chloride | 0.20 g |
|   | Acid | 25 ml of 25% aqueous HCl solution mixed with 100 ml of isopropanol | 2 ml |

Example 2
Testing of the Behavior of Special Reagents

The behavior of the following reagents A to E, that can be used according to the invention, was examined in this example:

In this case, aqueous solutions of malonic dialdehyde were used as the "model urine," with concentrations of 10 $\mu$mol/l and 1.0 $\mu$mol/l, respectively. (Typical malonic dialdehyde concentrations in human urine are of the order of 0.5 to 5 $\mu$mol/l).

A solution of 100 mg of reagent (A to E) dissolved in 50 ml of isopropanol was used as the reagent solution, and a mixture of 25 ml of 25% aqueous HCl solution and 50 ml of isopropanol was used as the acid solution.

The test was carried out by mixing 1 ml of the test solution with 1 ml of reagent solution and 1 ml of acid solution. The mixture thus obtained was vigorously shaken in a sealed vessel and allowed to stand at 22° C. The colorations that occurred were then determined once after 15 to 20 minutes, then again after 60 minutes, and are indicated in the following Table 2.

The individual colorations were in this case determined by comparison with the HSKTM standard color tables and fans ("K" screen fans, 1993 Issue, Hostmann-Steinberg, Celle, sales through HKVdruck GmbH, Stuttgart), the color code (e.g. "45K") and saturation or brightness stage (e.g. 60%) at a grey stage of 0% being indicated in Table 2.

Reagents A and B give red color tones, reagent C gives a blue-grey color tone and reagents D and E give blue color tones.

TABLE 2

| | Malonic dialdehyde concentration | | | |
|---|---|---|---|---|
| | 10 $\mu$mol/l Reaction time | | 1.0 $\mu$mol/l Reaction time | |
| Reagent | 15 to 20 mins. | 60 mins. | 15 to 20 mins. | 60 mins. |
| A | 27K (100%) | 27K (100%) | 27K (100%) | 27K (100%) |
| B | 31K/29K* (100%) | 31K/29K* (100%) | 31K/33K* (100%) | 31K/33K* (100%) |
| C | 36K (100%) | 82K (40%) | 28K (100%) | 1K (60%) |
| D | 45K (60%) | 45K (100%) | 26K (20%) | 34K (60%) |
| E | 40K (80%) | 43K (100%) | 40K (10%) | 40K (50%) |

*In the case of these samples, the color tone was between two colors in the comparison scale.

The following graduations of the reaction speed (in descending order) or the individual reagents were established on the basis of these tests:

(a) at a malonic dialdehyde concentration of 10 $\mu$mol/l:

A=B=C>D>E (b) at a malonic dialdehyde concentration of 1.0 $\mu$mol/l:

A>B>C>>D>E

In a similar test with variation of the acid used (according to Example 1, Variant 2; malonic dialdehyde concentration= 10 $\mu$mol/l), the following graduation of the reaction speed (in descending order) was determined: hydrochloric acid>>trichloroacetic acid>oxalic acid>citric acid.

Example 3
Monitoring of Redox Status when Administering Micronutrients with an Oxidative Action Starting from urine samples not subject to oxidative load, with yellow colorations of varying intensities (e.g., which may correspond to the HKS™ reference colors 1K, 3K and 5K; see the data given in Example 2), and using malonic dialdehyde dilution series, a color scale was produced for each initial urine color, its graduations being denoted in the following by I (low oxidative load), II (medium oxidative load), and III (high oxidative load).

A first-dimension color scale or "urine color control scale" is developed to account for the varying yellow coloration of urine (using, e.g., the HKS™ reference colors). The "urine color control scale" provides a continuous or punctuated spectrum of yellow, representative of the varying yellow colorations of urine. The "urine color control scale" eliminates the potentially confounding effect that the initial color of a tested urine might have on the results achieved using the methods or kits of the invention. The "urine color control scale" is generated, for example, by collecting a number of urine samples from a representative range of human subjects, preferably a number of human subjects that can provide a set of urine samples collectively ranging in color from relatively pale to relatively intense yellow. Alternatively, the "urine color control scale" is generated by adding varying quantities of a yellow dye to a solvent, preferably water (e.g., by serial dilution), in order to produce a series of solutions with varying yellow intensities that approximately matches the various yellow colorations of urine. Preferably, these dye solutions collectively range in intensity from relatively pale to the relatively intense yellow. Alternatively, the "urine color control scale" is generated by using yellow filters ranging in intensity from the relatively pale to the relatively intense yellow colors characteristic of urine.

A second-dimension color scale, or "reaction color scale," is developed from each member of the urine color control scale by holding constant the initial color intensity of a solution while varying the concentration of MDA (malonic dialdehyde). Individually, a second-dimension reaction color scale (each individual reaction color scale being associated with a single member of the first-dimension, or urine color control, scale) accounts for the varying concentrations of MDA in urine of a particular color intensity, with the range of MDA concentrations being indicative of the range of low (I) to high (III) oxidative loads in an organism. Collectively, the reaction color scales include the first-dimension urine color control scale, thereby accounting for both the varying initial coloration of urines amenable to testing and the color of products resulting from reactions of varying concentrations of MDA.

The "reaction color scale" is generated, for example, by varying the concentration of MDA in aliquots of a single fluid of determinable color intensity, including a lack of coloration such as is found with water, a preferred fluid. MDA of differing concentrations is generated by any method known in the art. For example, a known MDA concentration may be diluted by, e.g, serial dilution. This results in a linear dilution series or a non-linear dilution series, such as serial dilutions that progressively reduce the MDA concentrations by 50%, 90%, or any other suitable increment. It will be recognized by those of skill in the art that the incremental variation need not be constant. One of ordinary skill in the art will be able to use any method known in the art to generate a series of varying MDA concentrations that correspond to the lowest to highest concentrations of relevant substances (i.e., substances reactive with at least one each of the reagents and acids disclosed herein to yield colored products) found in human urine. Typically, the relevant substance is MDA itself, and the following description is presented in terms of MDA. Alternatively, reaction color scales are prepared, for example, using urine, recognizing that the original concentration of MDA in the urine is unknown.

"Reaction color scales" can also be generated, for example, by preparing a series of varying MDA concentrations in a MDA-free solvent, preferably water, by adding either linear or non-linear concentrations of MDA to aliquots of the solvent. Similarly, urine can also be used to prepare a MDA concentration series by adding varying MDA concentrations to individual urine aliquots, again recognizing that the original concentration of MDA in the urine is unknown and, thus, the final concentration is not known with complete precision.

If urine is used as the solvent for the above-described control color scales, the final concentration of MDA is not precisely known because the urine contains an unknown variable of MDA concentration. However, the effect of this imprecision is minimized by realizing that, given a linear correlation between the concentration of MDA and a certain color intensity generated by reacting MDA with a particular reagent (e.g., Example 1), one of ordinary skill in the art can determine the color intensity change per unit value of MDA. By way of further explanation, assume a baseline color, A, attributable to the MDA in the pure urine solvent. The reaction color attributable to that urine when supplemented by a known concentration of MDA gives a value X. The formula (X−A)/[concentration of MDA added] is equal to the color intensity change per unit value of MDA. Using this formula, one can control for the color contribution attributable to the added MDA, thereby determining the concentration of MDA in the urine.

Reagent and acid are then added to each member of the various MDA concentration series described above and reactions are allowed to proceed until reaction product of stable color is observed. The colors of these reaction products are due to both the initial color of the reaction mixture and the color attributable to the MDA therein. The resulting colors are then associated with particular concentrations of MDA in solutions of particular initial yellow intensities. One of ordinary skill in the art will recognize that the initial colorations of the reaction mixtures may be due to the natural colorations of particular urines, to modifications to the reaction mixture colorations by adding e.g., yellow dyes, by detecting the color of such reaction mixtures through color filters (e.g., yellow filters), or by using any means known in the art to approximate the various colorations of urine.

Morning urine samples from 61 healthy volunteers were first examined for their redox status, exactly the same procedure as in Example 1, Variant 2, being adopted. The test was carried out on the same morning of sampling. The following frequency of the individual load stages was recorded:

| | |
|---|---|
| I: | 41 subjects |
| II: | 15 subjects |
| III: | 5 subjects |

Moreover, the samples were tested for their pH value and ascorbic acid content using suitable, commercially available test strips, no correlation being established between these values and the redox status determined according to the invention.

A particular oxidative load exhibited by an individual can be either low, medium, or high. These oxidative loads correlate to specific concentration ranges of relevant substances (e.g., MDA) in urine. A low oxidative load (I) corresponds to a MDA concentration in urine ranging from greater than 0 to 0.5 μM. A medium oxidative load (II) corresponds to a MDA concentration in urine ranging from greater than 0.5 μM to 1.5 μM. A high oxidative load (III) corresponds to a MDA concentration in urine greater than 1.5 μM up to 3.0 μM or beyond.

Three subjects whose samples exhibited a high oxidative load (Stage III) in the first test were then administered a dose of a commercially available micro-nutrient preparation on the same day (day 1), after the first urine sampling, the preparation having the following anti-oxidatively acting components:

| | |
|---|---|
| Vitamin A: | 2500 I.E. = 0.75 g |
| Vitamin C: | 950 mg |
| Vitamin E: | 150 mg |
| Beta-carotin: | 15 mg | and the following trace elements required for the anti-oxidative action of different enzymes:

| | |
|---|---|
| Selenium: | 50 μg |
| Iron: | 0.8 mg |
| Zinc: | 10 mg |
| Manganese: | 2 mg |
| Copper: | 0.5 mg. |

On the morning of the following days (day 2 to day 4) urine samples were again taken from the three subjects, and examined as on the first day. However, the administration of the micro-nutrient preparation was not repeated on days 2 to 4. The results of the tests on these urine samples are indicated in the following Table 3.

TABLE 3

| Subject | Day 1 | Day 2 | Day 3 | Day 4 |
|---|---|---|---|---|
| 1 | III | I | II | III |
| 2 | III | I | II | II |
| 3 | III | II | III | III |

This test, particularly the low load established on the first day after administration of the anti-oxidatively acting preparation (Day 2), clearly shows that the kit or method according to the invention are suitable for evaluating the redox status.

What is claimed is:

1. A kit for determining a redox status in an organism, comprising:

(a) at least one reagent selected from the group of compounds with the general formula (I)

wherein $R_1$ is H or $C_1$–$C_{10}$-alkyl;

and wherein $R_2$ is independently selected from the group consisting of $C_1$–$C_{10}$-alkyl; NH; NHR; $NR_2$; NBCOR; OH; OR; OCOR; SH; SR; F; Cl; Br; $CF_3$; or $CCl_3$, and wherein each R is selected from the group consisting of $C_1$–$C_6$-alkyl;

and wherein $R_3$ and $R_4$ are independently selected from the group consisting of H; $C_1$–$C_{10}$-alkyl; $NH_2$; NHR; $NR_2$; NHCOR; OH; OR; OCOR; SH; SR; F; Cl; Br; $CF_3$; $CCl_3$; $C_6$–$C_{14}$-aryl; $C_6$–$C_{14}$-aryl, wherein the aryl group is substituted by one or more substituents selected from the group consisting of $C_1$–$C_6$-alkyl, $NH_2$, NHR, $NR_2$, NHCOR, OH, OR, OCOR, SH, SR, F, Cl, Br, $CF_3$ and $CCl_3$, and wherein each R is selected from the group consisting of $C_1$–$C_6$-alkyl;

(b) at least one acid; and (c) a color scale for visual color comparison, where the redox status of the organism to be analyzed is determinable from individual colors on the scale.

2. The kit according to claim 1, wherein the reagent is 2-methyl indole or 1,2-dimethyl indole.

3. The kit according to claim 1, wherein the acid is hydrochloric acid.

4. The kit according to claim 1, wherein the reagent is present in the form of a solution in at least one solvent.

5. The kit according to claim 4, wherein the concentration of the reagent in the solution is 0.1 to 50 mmol/l.

6. The kit according to claim 1, wherein the acid is present in the form of a solution in at least one solvent.

7. The kit according to claim 6, wherein the concentration of the acid in solution is 0.1 to 5.0 mol/l.

8. The kit according to claim 6, wherein the solvent comprises isopropanol.

9. The kit according to claim 1, wherein the reagent or a solution thereof is contained in a sealed container, which can be destroyed or opened by deliberate mechanical action, the reagent or a solution thereof is separate from the acid, and the reagent or solution thereof is arranged so that the reagent or solution thereof is capable of directly contacting the acid or a solution thereof and the urine sample as a result of the destruction or opening of the container.

10. The kit according to claim 1, wherein the acid or a solution thereof is contained in a sealed container, which can be destroyed or opened by deliberate mechanical action, the acid or a solution thereof is separate from the reagent, and the acid or a solution thereof is arranged so that the acid or solution thereof is capable of directly contacting the reagent or a solution thereof and the urine sample as a result of the destruction or opening of the container.

11. The kit according to claim 1, wherein the reagent is present in solid form.

12. The kit according to claim 11, wherein the reagent is present in the form of a mixture with a neutral carrier substance.

13. The kit according to claim 1, further comprising at least one of the following elements: a vessel for immediate receiving of the excreted urine and an analysis vessel in which a urine sample, the reagent and acid are brought into contact.

14. The kit according to claim 1, further comprising an analysis vessel in which the urine sample, the reagent, and the acid are brought into contact, wherein the color scale is connected to the analysis vessel so that the color comparison between the sample solution and the color scale can be carried out immediately and visually.

15. The kit according to claim 1, wherein the reagent and the acid are both incorporated into the test strip in solid form, wherein said test strip can be immersed directly in the sample to be analyzed.

16. The kit according to claim 15, wherein the acid is citric acid, oxalic acid, or trichloroacetic acid.

17. A method for determining a redox status in an organism, comprising the following steps:
(a) mixing a urine sample to be analyzed with
    (i) at least one reagent selected from the group of compounds with the general formula (I)

(I)

wherein $R_1$ is H or $C_1$–$C_{10}$-alkyl;
and wherein $R_2$ is independently selected from the group consisting of $C_1$–$C_{10}$-alkyl; $NH_2$; NHR; $NR_2$; NHCOR; OH; OR; OCOR; SH; SR; F; Cl; Br; $CF_3$; or $CCl_3$, and wherein each R is selected from the group consisting of $C_1$–$C_6$-alkyl;
and wherein $R_3$ and $R_4$ are independently selected from the group consisting of H; $C_1$–$C_{10}$-alkyl; $NH_2$; NHR; $NR_2$; NHCOR; OH; OR; OCOR; SE; SR; F; Cl; Br; $CF_3$; $CCl_3$; $C_6$–$C_{14}$-aryl; $C_6$–$C_{14}$-aryl, wherein the aryl group is substituted by one or more substituents selected from the group consisting of $C_1$–$C_6$-alkyl, $NH_2$, NHR, $NR_2$, NHCOR, OH, OR, OCOR, SH, SR, F, Cl, Br, $CF_3$ and $CCl_3$, and wherein each R is selected from the group consisting of $C_1$–$C_6$-alkyl; and
    (ii) at least one acid;
to obtain a mixed sample; and
(b) visually comparing the coloration of the mixed sample with a color scale, thereby determining a specific redox status of the organism.

18. The method according to claim 17, wherein the reagent is 2-methyl indole or 1,2-dimethyl indole.

19. The method according to claim 17, wherein the acid is hydrochloric acid.

20. The method according to claim 17, wherein the reagent is used in the form of a solution in at least one solvent.

21. The method according to claim 20, wherein the concentration of the reagent in the solution is 0.1 to 50 mmol/l.

22. The method according to claim 17, wherein the acid is used in the form of a solution in at least one solvent.

23. The method according to claim 22, wherein the concentration of the acid in the solution is 0.1 to 5.0 mol/l.

24. The method according to claim 22, wherein the solvent comprises isopropanol.

25. The method according to claim 17, wherein the reagent or a solution thereof is first contained in a sealed container, which can be destroyed or opened by deliberate mechanical action, the reagent or a solution thereof is separate from the acid, and the reagent or solution thereof is arranged so that the reagent or solution thereof is capable of directly contacting the acid or a solution thereof and the urine sample as a result of the destruction or opening of the container.

26. The method according to claim 17, wherein the acid or a solution thereof is contained in a sealed container, which can be destroyed or opened by deliberate mechanical action, the acid or a solution thereof is separate from the reagent, and the acid or a solution thereof is arranged so that the acid or solution thereof is capable of directly contacting the reagent or a solution thereof and the urine sample as a result of the destruction or opening of the container.

27. The method according to claim 17, wherein the reagent is used in a solid form.

28. The method according to claim 27, wherein the reagent is used in the form of a mixture with a neutral carrier substance.

29. The method according to claim 17, wherein the reagent and the acid are both used in solid form in a test strip which is immersed directly in the sample to be analyzed.

30. The method according to claim 29, wherein the acid is citric acid, oxalic acid, or trichloroacetic acid.

31. The kit according to claim 4, wherein the solvent comprises isopropanol.

32. The method according to claim 20, wherein the solvent comprises isopropanol.

33. A kit for determining redox status in an organism, comprising:
(a) at least one reagent selected from the group of compounds with the general formula (I)

(I)

wherein $R_1$ is H or $C_1$–$C_{10}$-alkyl;
and wherein $R_2$ is $C_1$–$C_{10}$-alkyl;
and wherein $R_3$ and $R_4$ are independently selected from the group consisting of H; $C_1$–$C_{10}$-alkyl; $NH_2$; NHR; $NR_2$; NHCOR; OH; OR; OCOR SH; SR; F; Cl; Br; $CF_3$; $CCl_3$; $C_6$–$C_{14}$-aryl; $C_6$–$C_{14}$-aryl, wherein the aryl group is substituted by one or more substituents selected from the group consisting of $C_1$–$C_6$-alkyl, $NH_2$, NHR, $NR_2$, NHCOR, OH, OR, OCOR, SH, SR, F, Cl, Br, $CF_3$, and $CCl_3$, and wherein each R is selected from the group consisting of $C_1$–$C_6$-alkyl;
(b) at least one acid; and
(c) a color scale for visual color comparison, where a certain redox status of the organism to be analyzed is determinable from individual colors on the scale.

34. A method for determining a redox status in an organism, comprising the following steps:
(a) mixing a urine sample to be analyzed with
    (i) at least one reagent selected from the group of compounds with the general formula (I)

(I)

wherein $R_1$ is H or $C_1$–$C_{10}$-alkyl;
and wherein $R_2$ is $C_1$–$C_{10}$-alkyl;
and wherein $R_3$ and $R_4$ are independently selected from the group consisting of H;
$C_1$–$C_{10}$-alkyl; $NH_2$; NHR; $NR_2$; NHCOR; OH; OR; OCOR; SH; SR; F; Cl; Br; $CF_3$; $CCl_3$; $C_6$–$C_{14}$-aryl; $C_6$–$C_{14}$-aryl, wherein the aryl group is substituted by one or more substituents selected from the group consisting of $C_1$–$C_6$-alkyl, $NH_2$, NHR, $NR_2$, NHCOR, OH, OR, OCOR, SH, SR, F, Cl, Br, $CF_3$ and $CCl_3$, and wherein each R is selected from the group consisting of $C_1$–$C_6$-alkyl; and (ii) at least one acid;

to obtain a mixed sample; and (b) visually comparing the coloration of the mixed sample with a color scale, thereby determining a specific redox status of the organism.

* * * * *